US012661090B2

(12) United States Patent
Kwon et al.

(10) Patent No.: US 12,661,090 B2
(45) Date of Patent: Jun. 23, 2026

(54) ULTRASONIC IMAGE PROVIDING METHOD AND LEARNING ALGORITHM THEREOF

(71) Applicant: SAMSUNG MEDISON CO., LTD., Hongcheon-gun (KR)

(72) Inventors: Ja Young Kwon, Seoul (KR); Ye Jin Park, Seoul (KR); Jin Yong Lee, Hongcheon-Gun (KR); Sung Wook Park, Hongcheon-Gun (KR); Jin Ki Park, Hongcheon-Gun (KR); Dong Eun Lee, Hongcheon-Gun (KR); Ji Hun Lee, Hongcheon-Gun (KR); Kwang Yeon Choi, Hongcheon-Gun (KR)

(73) Assignee: SAMSUNG MEDISON CO., LTD., Hongcheon-Gun (KR)

( * ) Notice: Subject to any disclaimer, the term of this patent is extended or adjusted under 35 U.S.C. 154(b) by 143 days.

(21) Appl. No.: 18/271,118

(22) PCT Filed: Aug. 19, 2021

(86) PCT No.: PCT/KR2021/011063
§ 371 (c)(1),
(2) Date: Jul. 6, 2023

(87) PCT Pub. No.: WO2022/177083
PCT Pub. Date: Aug. 25, 2022

(65) Prior Publication Data
US 2024/0074736 A1      Mar. 7, 2024

(30) Foreign Application Priority Data

Feb. 16, 2021    (KR) ........................ 10-2021-0020741

(51) Int. Cl.
*A61B 8/00* (2006.01)
*G06T 7/00* (2017.01)

(52) U.S. Cl.
CPC ............ *A61B 8/5223* (2013.01); *A61B 8/465* (2013.01); *A61B 8/469* (2013.01); *A61B 8/523* (2013.01);
(Continued)

(58) Field of Classification Search
CPC ....... A61B 8/5223; A61B 8/465; A61B 8/469; A61B 8/523; G06T 7/0012; G06T 2207/10132
See application file for complete search history.

(56) References Cited

U.S. PATENT DOCUMENTS 6,402,693 B1    6/2002 Emery
6,656,120 B2    12/2003 Lee et al.
(Continued)

FOREIGN PATENT DOCUMENTS

CN        109044398 A    12/2018
CN        116737098 A    9/2023
(Continued)

OTHER PUBLICATIONS

Extended European Search Report dated Nov. 20, 2024, issued in corresponding European Patent Application No. 21926882.8.
(Continued)

*Primary Examiner* — Dixomara Vargas
(74) *Attorney, Agent, or Firm* — Morgan Lewis & Bockius LLP

(57) ABSTRACT

An ultrasonic image providing method of the present disclosure includes: receiving ultrasonic images; measuring a plurality of similarities for a plurality of measurement items for at least one of the ultrasonic images; comparing the plurality of similarities with corresponding default thresh-
(Continued)

olds, respectively; when none of the plurality of similarities is greater than the corresponding default threshold, selecting a measurement item maintaining the greatest similarity among the plurality of similarities for a reference time; and providing an ultrasonic image for the selected measurement item as an ultrasonic image.

19 Claims, 15 Drawing Sheets

(52) U.S. Cl.
CPC .. *G06T 7/0012* (2013.01); *G06T 2207/10132* (2013.01); *G06T 2207/20081* (2013.01)

(56) References Cited

U.S. PATENT DOCUMENTS

| | | | |
|---|---|---|---|
| 6,882,970 B1 * | 4/2005 | Garner | G10L 15/26 |
| | | | 707/E17.103 |
| 8,073,215 B2 | 12/2011 | Lu et al. | |
| 8,092,388 B2 | 1/2012 | Park et al. | |
| 9,734,626 B2 | 8/2017 | Jago et al. | |
| 10,083,372 B2 | 9/2018 | Li et al. | |
| 10,346,989 B2 | 7/2019 | Xu et al. | |
| 10,349,918 B2 | 7/2019 | Lee et al. | |
| 10,395,346 B2 | 8/2019 | Lee et al. | |
| 10,702,248 B2 | 7/2020 | Vignon et al. | |
| 11,298,109 B2 | 4/2022 | Yao et al. | |
| 11,331,079 B2 | 5/2022 | Yu et al. | |
| 2008/0049994 A1 * | 2/2008 | Rognin | G06T 7/35 |
| | | | 382/128 |
| 2010/0185090 A1 | 7/2010 | Suzuki et al. | |
| 2012/0116237 A1 * | 5/2012 | Harks | A61B 5/0084 |
| | | | 600/508 |
| 2015/0201909 A1 * | 7/2015 | Yamamoto | A61B 8/585 |
| | | | 600/442 |
| 2015/0250446 A1 | 9/2015 | Kanayama | |
| 2016/0140770 A1 * | 5/2016 | Jönsson | G06T 15/08 |
| | | | 345/420 |
| 2016/0171158 A1 * | 6/2016 | Park | G06T 11/60 |
| | | | 715/771 |
| 2018/0301216 A1 | 10/2018 | Nakamura | |
| 2019/0155329 A1 | 5/2019 | Lee et al. | |
| 2019/0343489 A1 * | 11/2019 | Matsunaga | A61B 6/5247 |
| 2020/0082205 A1 * | 3/2020 | Takeshima | G06F 18/22 |
| 2021/0042913 A1 * | 2/2021 | Takeshima | G16H 30/20 |
| 2021/0378638 A1 * | 12/2021 | Sutton | A61B 8/546 |
| 2022/0058804 A1 * | 2/2022 | Carmi | G16H 30/40 |

FOREIGN PATENT DOCUMENTS

| | | |
|---|---|---|
| EP | 3590436 A1 | 1/2020 |
| EP | 3106095 B1 | 1/2021 |
| JP | 2006-102548 A | 4/2006 |
| JP | 2013-198635 A | 10/2013 |
| JP | 2014-171755 A | 9/2014 |
| JP | 6721945 B2 | 7/2020 |
| JP | 6915969 B2 | 8/2021 |
| JP | 6996303 B2 | 1/2022 |
| KR | 10-0527315 B1 | 11/2005 |
| KR | 10-2017-0045695 A | 4/2017 |
| KR | 10-2017-0074603 A | 6/2017 |
| KR | 10-2021-0038461 A | 4/2021 |
| KR | 10-2022-0166699 A | 12/2022 |
| WO | 2009/013871 A1 | 1/2009 |

OTHER PUBLICATIONS

International Search Report and Written Opinion dated Jan. 19, 2022 issued in International Patent Application No. PCT/KR2021/011063 (with English translation).
Office Action dated Oct. 24, 2025 issued in the corresponding Korean Patent Application No. 10-2021-0020741 with the English translation. (Note: US 2019/0343489 A1, and EP 3590436 A1 already submitted.).

* cited by examiner

Figure 6:
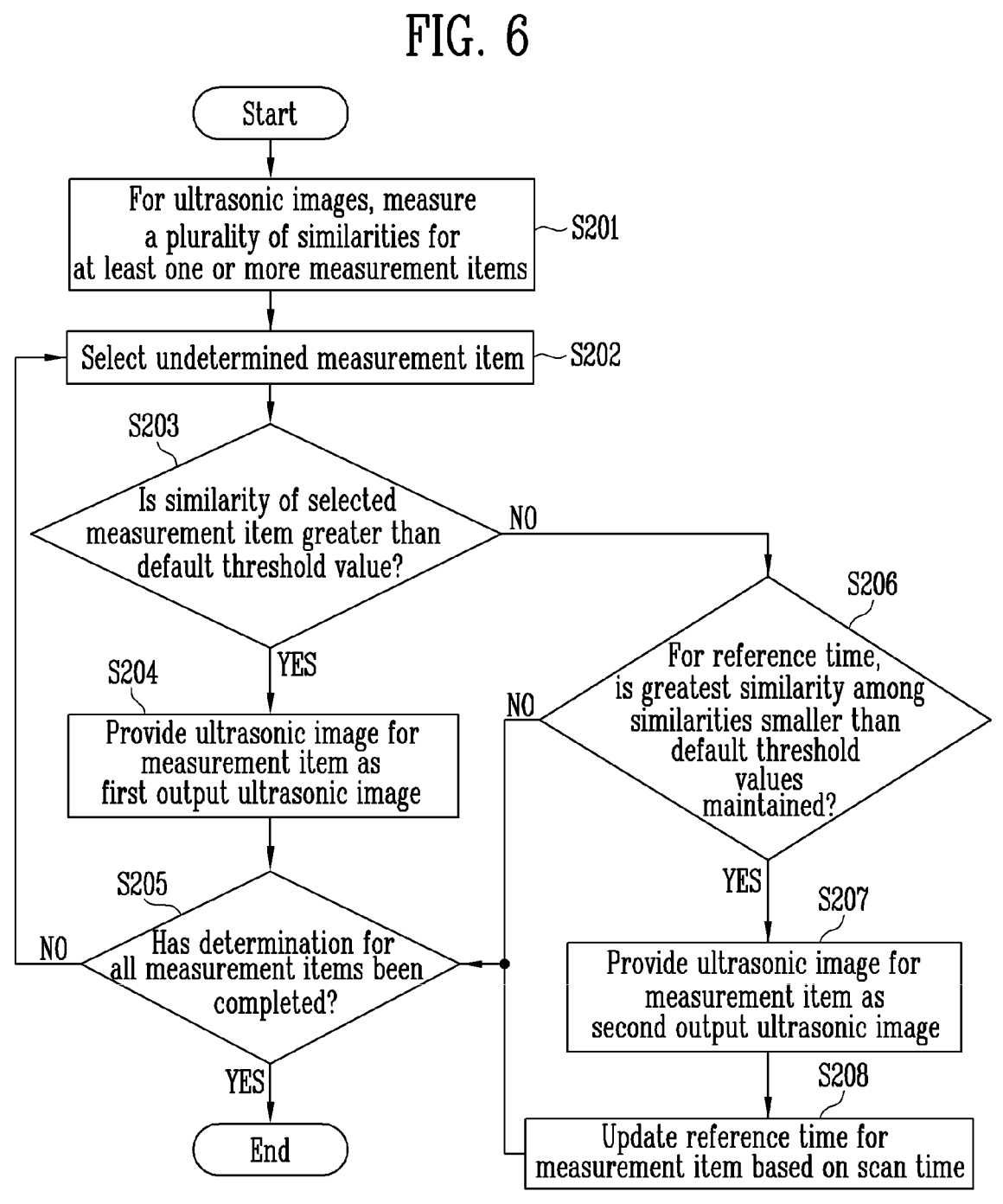

Start

For ultrasonic images, measure a plurality of similarities for at least one or more measurement items — S201

Select undetermined measurement item — S202

S203

Is similarity of selected measurement item greater than default threshold value? — NO

YES

S204

Provide ultrasonic image for measurement item as first output ultrasonic image

S205

Has determination for all measurement items been completed? — NO

YES

End

S206

For reference time, is greatest similarity among similarities smaller than default threshold values maintained? — NO

YES

S207

Provide ultrasonic image for measurement item as second output ultrasonic image

S208

Update reference time for measurement item based on scan time

FIG. 9

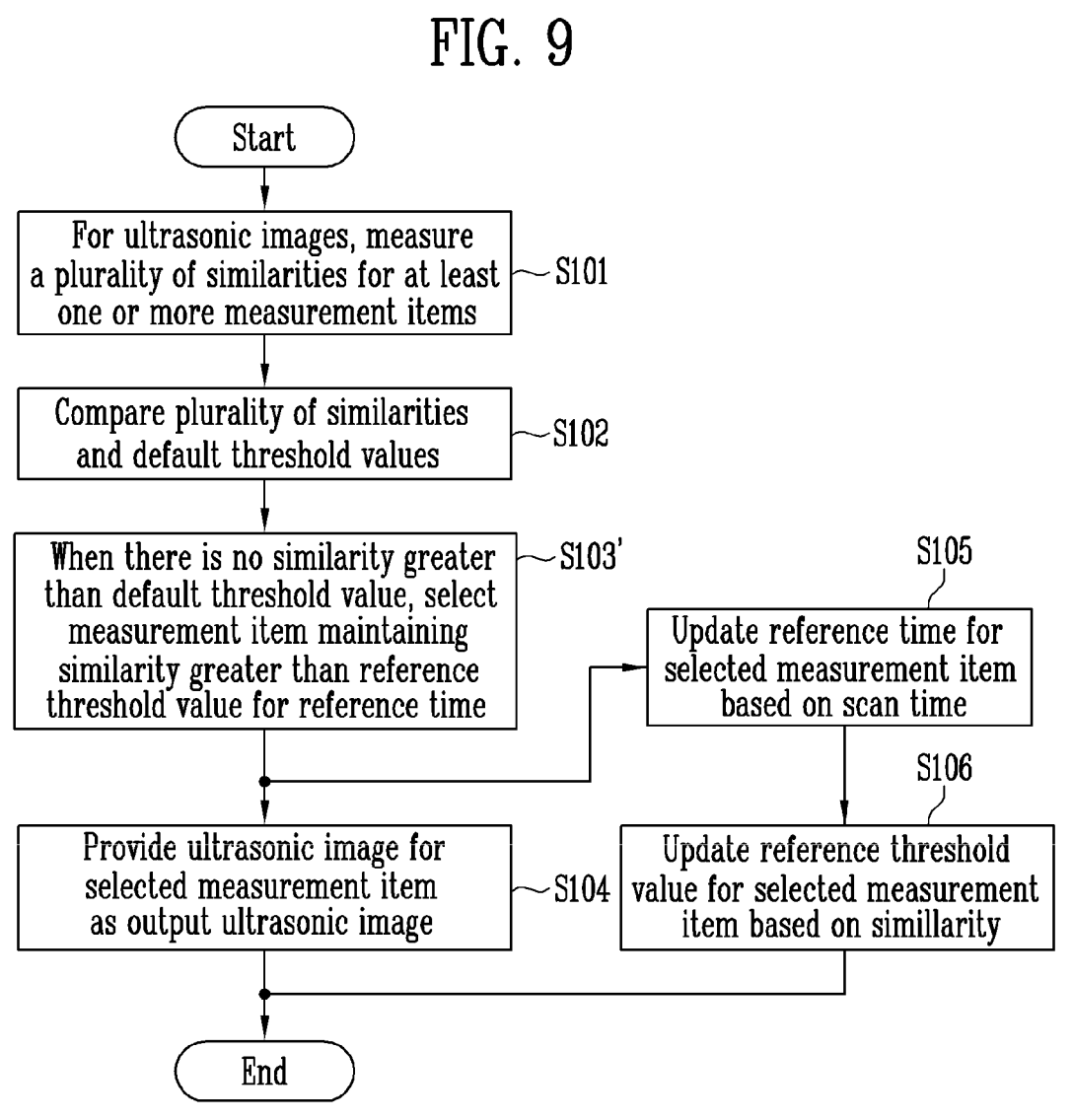

( Start )

For ultrasonic images, measure
a plurality of similarities for at least ~S101
one or more measurement items Compare plurality of similarities ~S102
and default threshold values When there is no similarity greater ~S103'
than default threshold value, select
measurement item maintaining
similarity greater than reference
threshold value for reference time

S105

Update reference time for
selected measurement item
based on scan time

S106

Provide ultrasonic image for
selected measurement item ~S104
as output ultrasonic image Update reference threshold
value for selected measurement
item based on simillarity ( End )

FIG. 11

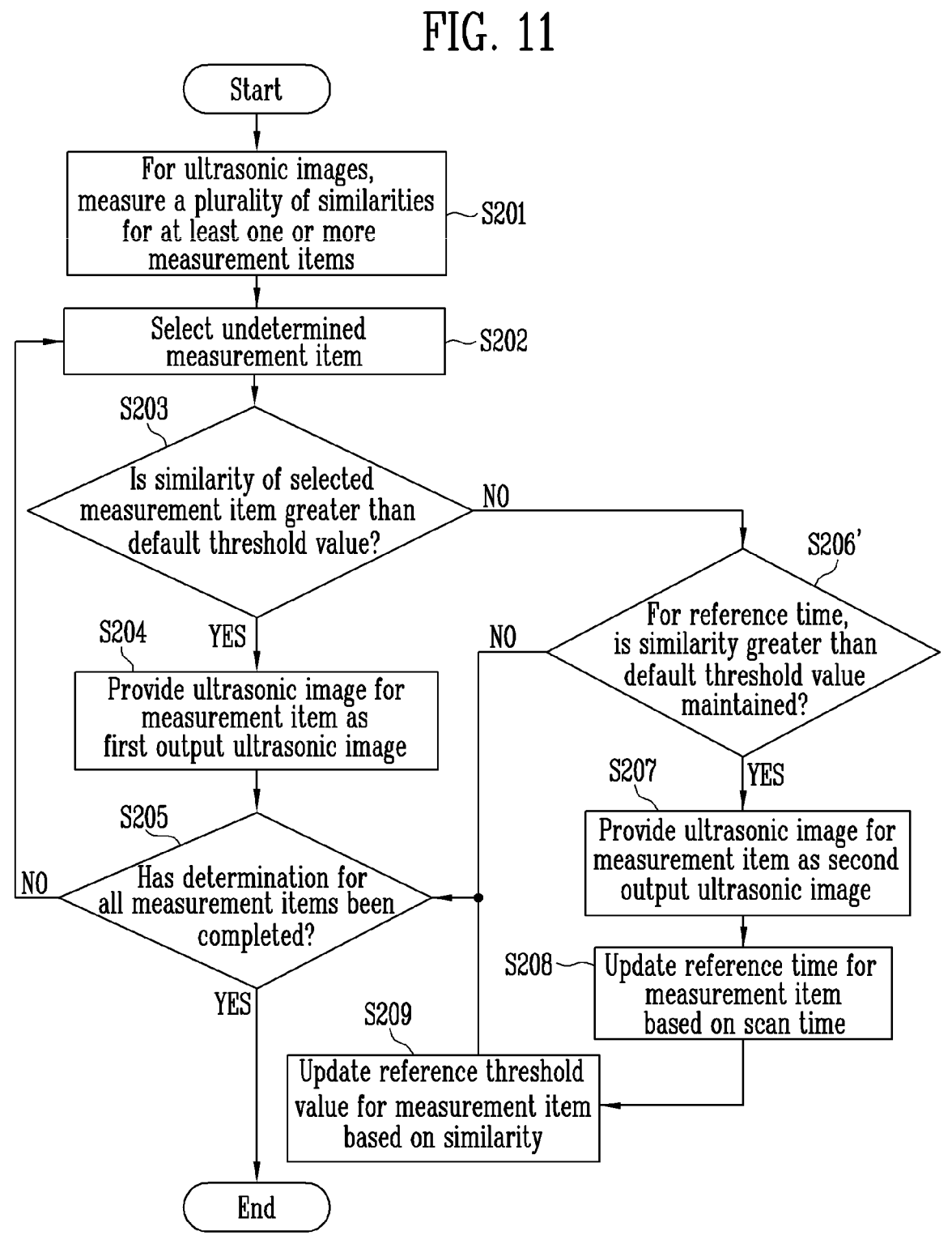

Start

For ultrasonic images,
measure a plurality of similarities
for at least one or more
measurement items — S201

Select undetermined
measurement item — S202

S203

Is similarity of selected
measurement item greater than
default threshold value? — NO

S204  YES

Provide ultrasonic image for
measurement item as
first output ultrasonic image

S206'

For reference time,
is similarity greater than
default threshold value
maintained? — NO

S207  YES

Provide ultrasonic image for
measurement item as second
output ultrasonic image

S208 — Update reference time for
measurement item
based on scan time

S205

Has determination for
all measurement items been
completed? — NO

YES

S209

Update reference threshold
value for measurement item
based on similarity

End

ULTRASONIC IMAGE PROVIDING METHOD AND LEARNING ALGORITHM THEREOF

CROSS-REFERENCE OF RELATED APPLICATIONS

This application is the U.S. National Phase under 35 U.S.C. § 371 of International Patent Application No. PCT/KR2021/011063, filed on Aug. 19, 201, which in turn claims the benefit of Korean Application No. 10-2021-0020741, filed on Feb. 16, 2021, the entire disclosures of which applications are incorporated by reference herein.

TECHNICAL FIELD

The present disclosure relates to an ultrasonic image providing method and a learning algorithm thereof.

BACKGROUND ART

An ultrasound diagnosis apparatus may, by irradiating an ultrasonic signal generated from a transducer of a probe to an object, and receiving and image processing a signal reflected from the object, provide at least one ultrasonic image for measurement items corresponding to the length, circumference, and the like of the object.

In general, the ultrasonic image represents a cross-section of the object, and a cross-section selection criterion for measuring the measurement item may be different for each user.

Algorithms for automatically selecting ultrasonic images suitable for the measurement items have been proposed, but there is a problem in that various cross-section selection criteria of users are not reflected because only a standardized cross-section selection criterion is presented.

DETAILED DESCRIPTION OF INVENTION

Technical Problem

An technical object to be achieved is to provide an ultrasonic image providing method capable of automatically providing ultrasonic images for measurement items by reflecting various cross-section selection criteria of users and a learning algorithm thereof.

Technical Solution

An ultrasonic image providing method according to an aspect of the present disclosure includes: for ultrasonic images, measuring a plurality of similarities for at least one or more measurement items; comparing the plurality of similarities with a plurality of corresponding default threshold values, respectively; when none of the plurality of similarities is greater than the corresponding default threshold value, selecting a measurement item maintaining the greatest similarity among the plurality of similarities for a reference time; and providing an ultrasonic image for the selected measurement item as an output ultrasonic image.

The ultrasonic image providing method may further include updating the reference time for the selected measurement item based on a scan time for which the greatest similarity is maintained.

The reference time for each of the measurement items may be different from each other.

The ultrasonic image providing method may further include, for the selected measurement item, when an ultrasonic image having a higher similarity than the greatest similarity is added, updating the output ultrasonic image with the added ultrasonic image.

The ultrasonic image providing method may further include, for the provided output ultrasonic image, providing an indicator indicating that the similarity of the selected measurement item is lower than the default threshold value.

An ultrasonic image providing method according to an aspect of the present disclosure includes: for ultrasonic images, measuring a plurality of similarities for at least one or more measurement items; comparing the plurality of similarities with a plurality of corresponding default threshold values, respectively; providing a first ultrasonic image for a first measurement item having a first similarity greater than a first default threshold value as a first output ultrasonic image; and after the first output ultrasonic image is provided, providing a second ultrasonic image for a second measurement item maintaining a second similarity which is greatest among similarities smaller than the default threshold values for a reference time as a second output ultrasonic image.

The ultrasonic image providing method may further include updating the reference time for the second measurement item based on a scan time for which the second similarity is maintained.

The reference time for each of the measurement items may be different from each other.

The ultrasonic image providing method may further include, for the first measurement item, when an ultrasonic image having a higher similarity than the first similarity is added, updating the first output ultrasonic image with the added ultrasonic image.

The ultrasonic image providing method may further include, for the second measurement item, when an ultrasonic image having a higher similarity than the second similarity is added, updating the second output ultrasonic image with the added ultrasonic image.

The ultrasonic image providing method may further include, for the first output ultrasonic image, providing a first indicator indicating that the first similarity is higher than the first default threshold value.

The ultrasonic image providing method may further include, for the second output ultrasonic image, providing a second indicator indicating that the second similarity is lower than the second default threshold value.

An ultrasonic image providing method according to an aspect of the present disclosure includes: for ultrasonic images, measuring a plurality of similarities for at least one or more measurement items; comparing the plurality of similarities with a plurality of corresponding default threshold values, respectively; when none of the plurality of similarities is greater than the corresponding default threshold value, selecting a measurement item maintaining a similarity greater than a reference threshold value for a reference time; and providing an ultrasonic image for the selected measurement item as an output ultrasonic image.

The ultrasonic image providing method may further include updating the reference time for the selected measurement item based on a scan time for which the similarity of the selected measurement item is maintained.

The ultrasonic image providing method may further include updating the reference threshold value for the selected measurement item based on the similarity of the selected measurement item.

The reference threshold value may be smaller than the default threshold value at both a point in time before the update and a point in time after the update.

The reference time and the reference threshold value for each of the measurement items nay be different from each other.

The ultrasonic image providing method may further include, for the selected measurement item, when an ultrasonic image having a higher similarity than the similarity is added, updating the output ultrasonic image with the added ultrasonic image.

The ultrasonic image providing method may further include, for the provided output ultrasonic image, providing an indicator indicating that the similarity of the selected measurement item is lower than the default threshold value.

An ultrasonic image providing method according to an aspect of the present disclosure includes: for ultrasonic images, measuring a plurality of similarities for at least one or more measurement items; comparing the plurality of similarities with a plurality of corresponding default threshold values, respectively; providing a first ultrasonic image for a first measurement item having a first similarity greater than a first default threshold value as a first output ultrasonic image; and after the first ultrasonic image is provided, providing a second ultrasonic image for a second measurement item maintaining a second similarity which is greater than a reference threshold value and smaller than a second default threshold value for a reference time as a second output ultrasonic image.

The ultrasonic image providing method may further include updating the reference time for the second measurement item based on a scan time for which the second similarity is maintained.

The ultrasonic image providing method may further include updating the reference threshold value for the second measurement item based on the second similarity.

The reference threshold value may be smaller than the default threshold value at both a point in time before the update and a point in time after the update.

The reference time and the reference threshold value for each of the measurement items may be different from each other.

The ultrasonic image providing method may further include, for the first measurement item, when an ultrasonic image having a higher similarity than the first similarity is added, updating the first output ultrasonic image with the added ultrasonic image.

The ultrasonic image providing method may further include, for the second measurement item, when an ultrasonic image having a higher similarity than the second similarity is added, updating the second output ultrasonic image with the added ultrasonic image.

The ultrasonic image providing method may further include, for the first ultrasonic image, providing a first indicator indicating that the first similarity is higher than the first default threshold value.

The ultrasonic image providing method may further include, for the second ultrasonic image, providing a second indicator indicating that the second similarity is lower than the second default threshold value.

A non-transitory recording medium on which a learning algorithm is recorded according to an aspect of the present disclosure is a non-transitory recording medium on which a learning algorithm including at least one hidden layer between an input layer and an output layer is recorded, wherein the learning algorithm includes: receiving ultrasonic images as first inputs of the input layer; receiving information about ultrasonic images which maintain a similarity for a first reference time among the ultrasonic images as a second input of the input layer; and based on the first inputs and the second input, providing whether the ultrasonic images include at least one or more measurement items as a first output of the output layer.

The first reference time may be information about a first user among a plurality of users, and the learning algorithm may further include modifying the hidden layer by receiving first reward information of the first user as feedback for the first output.

The learning algorithm may further include: receiving information about ultrasonic images which maintain a similarity for a second reference time among the ultrasonic images as a third input of the input layer; and based on the first inputs and the third input, providing whether the ultrasonic images include at least one or more measurement items as a second output of the output layer.

The second reference time may be information about a second user among the plurality of users, and the learning algorithm may further include modifying the hidden layer by receiving second reward information of the second user as feedback for the second output.

The learning algorithm may further include updating the first reference time based on a scan time for which the similarity is maintained.

The learning algorithm may further include updating the first reference time based on a difference between a point in time when the last image is input and a point in time when the first image is input among the ultrasonic images which maintain the similarity.

Advantageous Effects

An ultrasonic image providing method and a learning algorithm thereof according to the present disclosure can automatically provide ultrasonic images for measurement items by reflecting various cross-section selection criteria of users.

DESCRIPTION OF DRAWINGS

FIGS. 2A to 2C are diagrams illustrating an ultrasound diagnosis apparatus according to an embodiment.

FIGS. 5 and 6 are diagrams illustrating an ultrasonic image providing method according to another embodiment of the present disclosure.

FIGS. 8 and 9 are diagrams illustrating an ultrasonic image providing method according to another embodiment of the present disclosure.

FIGS. 10 and 11 are diagrams illustrating an ultrasonic image providing method according to another embodiment of the present disclosure.

MODES OF THE INVENTION

Figure 1:
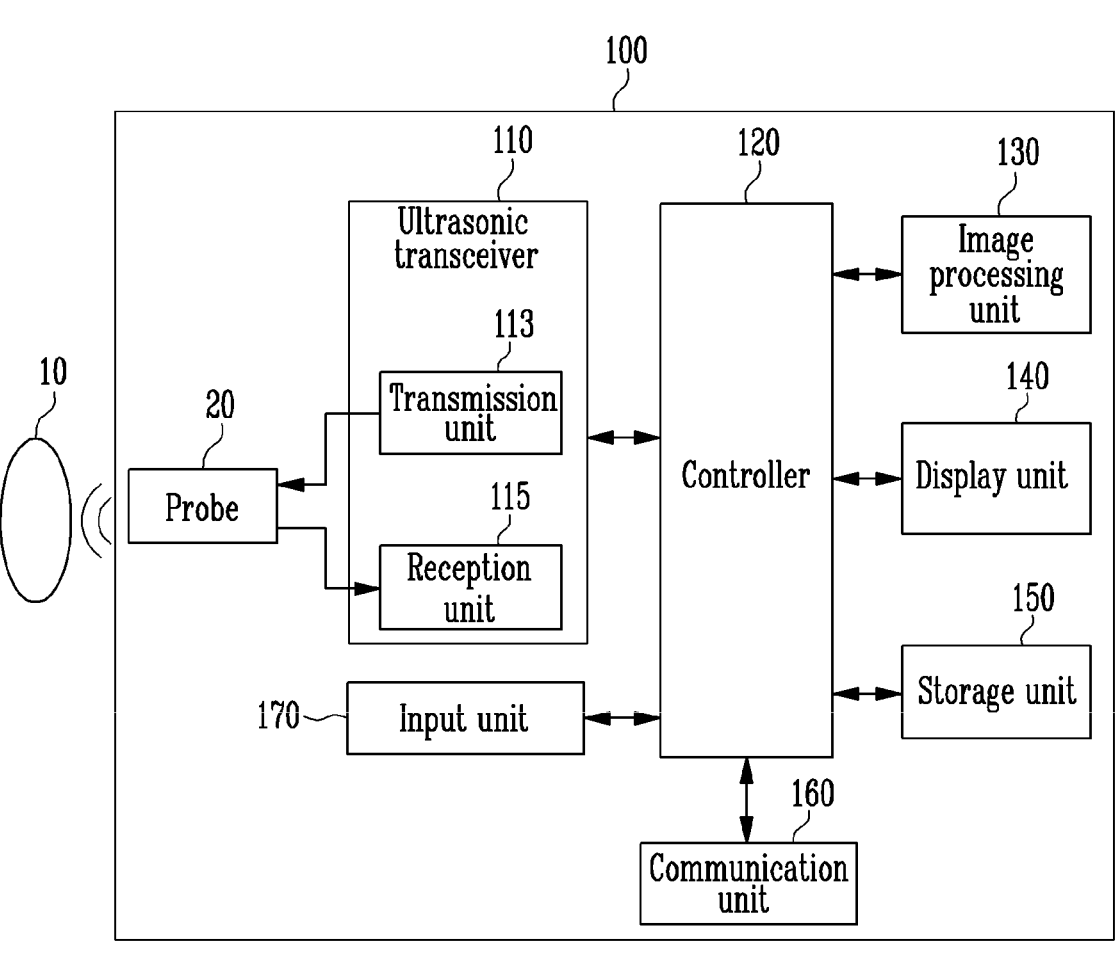
FIG. 1 is a block diagram illustrating a configuration of an ultrasound diagnosis apparatus according to an embodiment.

Hereinafter, various embodiments of the present disclosure will be described in detail with reference to the accompanying drawings so that those skilled in the art can easily carry out the present disclosure. The present disclosure may be implemented in various different forms and is not limited to the embodiments described herein.

In order to clearly describe the present disclosure, parts irrelevant to the description are omitted, and the same reference numerals are assigned to the same or similar components throughout the specification. Therefore, the reference numerals described above may be used in other drawings as well.

In addition, since size and thickness of each component shown in the drawings are arbitrarily shown for convenience of explanation, the present disclosure is not necessarily limited to those shown. In the drawing, the thickness may be exaggerated to clearly express various layers and regions.

In addition, the expression "the same" in the description may mean "substantially the same". In other words, it may be the same to the extent that those skilled in the art can understand that it is the same. Other expressions may also be expressions in which "substantially" is omitted.

The present specification clarifies the scope of the present disclosure, explains the principles of the present disclosure, and discloses embodiments so that those skilled in the art can carry out the present disclosure. The disclosed embodiments may be implemented in various forms.

Throughout the specification, when a part is said to be "connected" to another part, this includes not only the case of being directly connected but also the case of being indirectly connected, and the indirect connection includes being connected through a wireless communication network.

In addition, terms used herein are used to describe embodiments, and are not intended to restrict and/or limit the disclosed disclosure. Singular expressions include plural expressions unless the context clearly dictates otherwise. In this specification, terms such as "comprise" or "have" are intended to designate that the features, numbers, steps, operations, components, parts, or combinations thereof described in the specification exist, and do not preclude the possibility of the presence or addition of one or more other features, numbers, steps, operations, components, parts, or combinations thereof.

In addition, terms including ordinal numbers such as "first" and "second" used herein may be used to describe various components, but the components are not limited by the terms, and the terms are only used for the purpose of distinguishing one component from another. For example, a first component may be termed a second component, and similarly, a second component may be termed a first component, without departing from the scope of the present disclosure.

In addition, terms such as "~ unit", "~ group", "~ block", "~ member", and "~ module" may mean a unit that processes at least one function or operation. For example, the terms may mean at least one hardware such as a field-programmable gate array (FPGA)/application specific integrated circuit (ASIC), at least one software stored in a memory, or at least one process processed by a processor.

A symbol attached to each step is used to identify the step, and these symbols do not indicate the order of each step, and each step may be performed in a different order from the specified order unless the specific order is clearly described in context.

In addition, in the present specification, an image may include a medical image acquired by a medical imaging device such as a magnetic resonance imaging (MRI) device, a computed tomography (CT) device, an ultrasonic imaging device, or an X-ray imaging device.

In addition, in the present specification, an "object" is a target to be photographed, and may include a human, an animal, or a part thereof. For example, the object may include a body part (organs or the like) or a phantom.

Throughout the specification, an "ultrasonic image" refers to an image of an object that is processed based on ultrasonic signals transmitted to and reflected from the object.

Hereinafter, the embodiments will be described in detail with reference to the accompanying drawings.

FIG. 1 is a block diagram illustrating a configuration of an ultrasound diagnosis apparatus 100 according to an embodiment. The ultrasound diagnosis apparatus 100 may include a probe 20, an ultrasonic transceiver 110, a controller 120, an image processing unit 130, a display unit 140, a storage unit 150, a communication unit 160, and an input unit 170.

The ultrasound diagnosis apparatus 100 may be implemented as a portable type as well as a cart type. Examples of a portable ultrasound diagnosis apparatus may include a smart phone, a laptop computer, a personal digital assistant (PDA), a tablet personal computer (PC), and the like including a probe and an application, but the present invention is not limited thereto.

The probe 20 may include a plurality of transducers. The plurality of transducers may transmit ultrasonic signals to an object 10 according to a transmission signal applied from a transmission unit 113. The plurality of transducers may receive ultrasonic signals reflected from the object 10 to form a reception signal. Further, the probe 20 may be implemented integrally with the ultrasound diagnosis apparatus 100 or may be implemented as a separate type in which the probe 20 is connected to the ultrasound diagnosis apparatus 100 in a wired or wireless manner. Further, the ultrasound diagnosis apparatus 100 may include one or more probes 20 according to an implementation form.

The controller 120 controls the transmission unit 113 to form a transmission signal to be applied to each of the plurality of transducers in consideration of the positions and focal points of the plurality of transducers included in the probe 20.

The controller 120 controls a reception unit 115 to convert a reception signal received from the probe 20 in an analog-to-digital conversion manner and to sum the digitally converted reception signal in consideration of the positions and focal points of the plurality of transducers, thereby generating ultrasonic data.

The image processing unit 130 generates an ultrasonic image using the ultrasonic data generated by the ultrasonic reception unit 115.

The display unit 140 may display the generated ultrasonic image and various pieces of information processed by the ultrasound diagnosis apparatus 100. The ultrasound diagnosis apparatus 100 may include one or more display units 140 according to an implementation form. Further, the display unit 140 may be implemented as a touch screen in combination with a touch panel.

The controller 120 may control the overall operation of the ultrasound diagnosis apparatus 100 and a signal flow between internal components of the ultrasound diagnosis apparatus 100. The controller 120 may include a memory that stores a program or data for performing a function of the ultrasound diagnosis apparatus 100 and a processor that processes the program or data. Further, the controller 120 may control the operation of the ultrasound diagnosis apparatus 100 by receiving a control signal from the input unit 170 or an external device.

The ultrasound diagnosis apparatus 100 may include the communication unit 160 and may be connected, through the communication unit 160, to an external device (for example, a server, a medical device, a portable device (a smart phone, a tablet PC, a wearable device, and the like)).

The communication unit 160 may include one or more components enabling communication with the external device and may include, for example, at least one of a short-range communication module, a wired communication module, and a wireless communication module.

The communication unit 160 may receive a control signal and data from the external device and transmit the received control signal to the controller 120 so that the controller 120 may control the ultrasound diagnosis apparatus 100 in response to the received control signal.

Alternatively, the controller 120 may transmit a control signal to the external device through the communication unit 160 so that the external device may be controlled in response to the control signal of the controller 120.

For example, the external device may process the data of the external device in response to the control signal of the controller received through the communication unit.

A program capable of controlling the ultrasound diagnosis apparatus 100 may be installed in the external device, and the program may include instructions for performing some or all of the operations of the controller 120.

The program may be installed in the external device in advance or may be installed by a user of the external device by downloading the program from a server that provides applications. The server that provides applications may include a recording medium in which the corresponding program is stored.

In addition, in a system including a server and a client device, the program may include a storage medium of the server or a storage medium of the client device. Alternatively, if there is a third device (smart phone, tablet PC, wearable device, etc.) that is communicatively connected to the server or client device, the program product may include a storage medium of the third device. Alternatively, the program may include a S/W program itself transmitted from the server to the client device or the third device or from the third device to the client device.

In this case, one of the server, the client device, and the third device may execute the program to perform the method according to the disclosed embodiments. Alternatively, two or more of the server, the client device, and the third device may execute the program to implement the method according to the disclosed embodiments in a distributed manner.

For example, a server (e.g., a cloud server or an artificial intelligence server) may execute a program stored in the server and control a client device communicatively connected to the server to perform a method according to the disclosed embodiments.

The storage unit 150 may store various types of data or programs for driving and controlling the ultrasound diagnosis apparatus 100, input/output, acquired the ultrasonic image and etc.

The input unit 170 may receive a user's input to control the ultrasound diagnosis apparatus 100. For example, the user's input may include an input for manipulating a button, a keypad, a mouse, a trackball, a jog switch, a knob, or the like, an input for touching a touchpad or a touch screen, a voice input, a motion input, and a bioinformation input (e.g., iris recognition or fingerprint recognition), but the present disclosure is not limited thereto.

An example of the ultrasound diagnosis apparatus 100 according to an embodiment will be described later through FIGS. 2A to 2C.

Figure 2A:
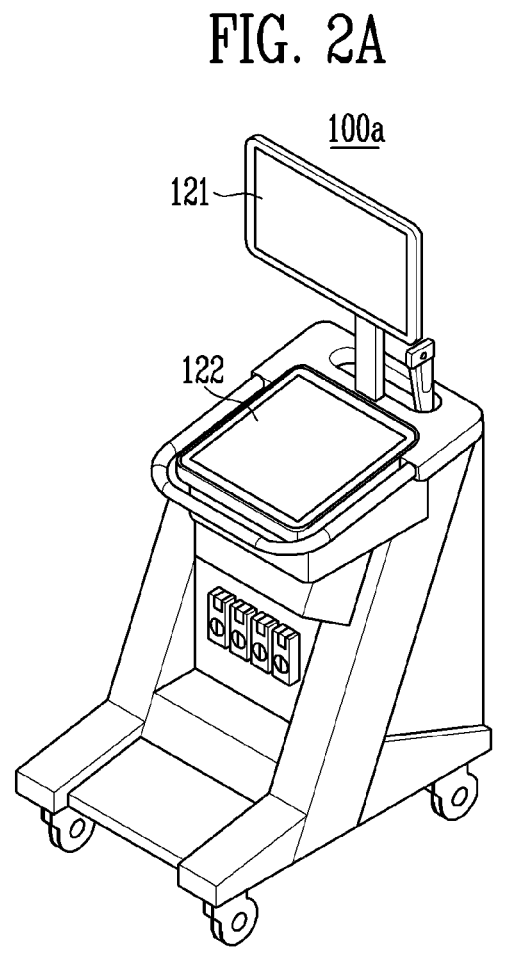
Figure 2B:
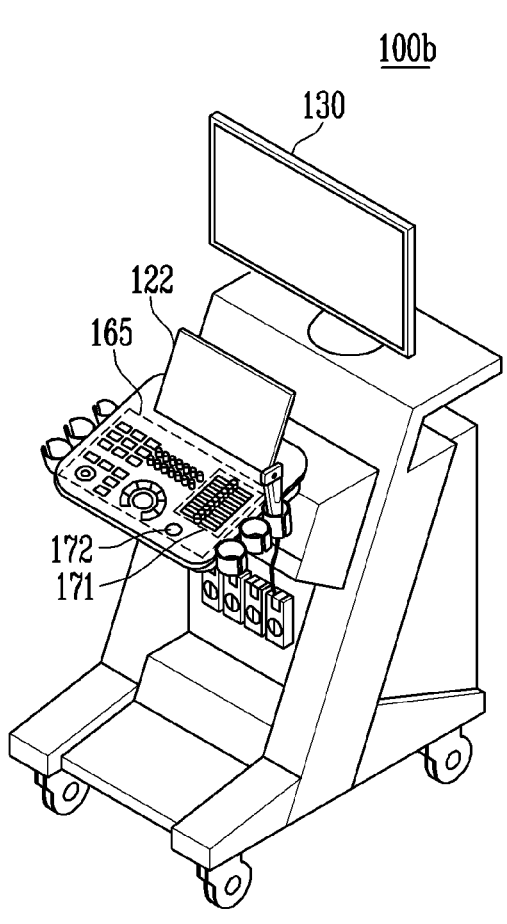
Figure 2C:
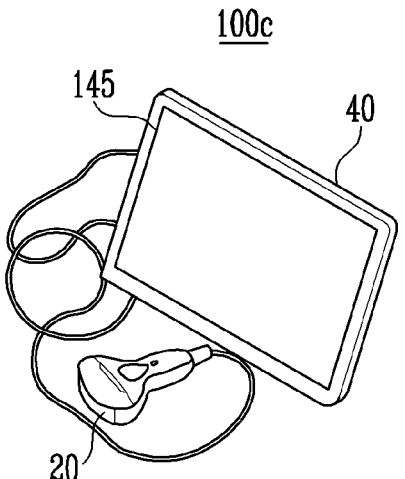

FIGS. 2A to 2C are diagrams illustrating an ultrasound diagnosis device according to an embodiment.

Referring to FIG. 2A and FIG. 2B, ultrasound diagnosis apparatuses 100*a* and 100*b* may each include a main display unit 121 and a sub display unit 122. One of the main display unit 121 and the sub display unit 122 may be implemented as a touch screen. The main display unit 121 and the sub display unit 122 may display the ultrasonic image or various pieces of information processed by the ultrasound diagnosis apparatuses 100*a* and 100*b*. Further, the main display unit 121 and the sub display unit 122 may be implemented as a touch screen and provide a graphical user interface (GUI) to receive data for controlling the ultrasound diagnosis apparatuses 100*a* and 100*b* from a user. For example, the main display unit 121 may display the ultrasonic image, and the sub display unit 122 may display a control panel for controlling the ultrasonic image in the form of the GUI. The sub display unit 122 may receive data for controlling the displaying of the image through the control panel displayed in the form of the GUI. The ultrasound diagnosis apparatuses 100*a* and 100*b* may control, using input control data, the displaying of the ultrasonic image displayed on the main display unit 121.

Referring to FIG. 2B, the ultrasound diagnosis apparatus 100*b* may further include a control panel 165 in addition to the main display unit 121 and the sub display unit 122. The control panel 165 may include a button, a trackball, a jog switch, a knob, and the like, and may receive data for controlling the ultrasound diagnosis apparatus 100*b* from the user. For example, the control panel 165 may include a time gain compensation (TGC) button 171, a freeze button 172, and the like. The TGC button 171 is a button for setting a TGC value for each depth of the ultrasonic image. Further, when detecting the input of the freeze button 172 while scanning the ultrasonic image, the ultrasound diagnosis apparatus 100*b* may maintain a state in which a frame image at a corresponding time point is displayed.

Meanwhile, inputs of the button, the trackball, the jog switch, the knob, and the like included in the control panel 165 may be provided to the GUI in the main display unit 121 or the sub display unit 122.

Referring to FIG. 2C, the ultrasound diagnosis apparatus 100*c* may be implemented as a portable type. Examples of a portable ultrasound diagnosis apparatus 100*c* may include a smart phone, a laptop computer, a PDA, a tablet PC, and the like including a probe and an application, but the present invention is not limited thereto.

The ultrasound diagnosis apparatus 100*c* may include the probe 20 and a main body 40, and the probe 20 may be connected to one side of the main body 40 in a wired or wireless manner. The main body 40 may include a touch screen 145. The touch screen 145 may display the ultrasonic image, various pieces of information processed by the ultrasound diagnosis apparatus, the GUI, and the like.

Figure 3:
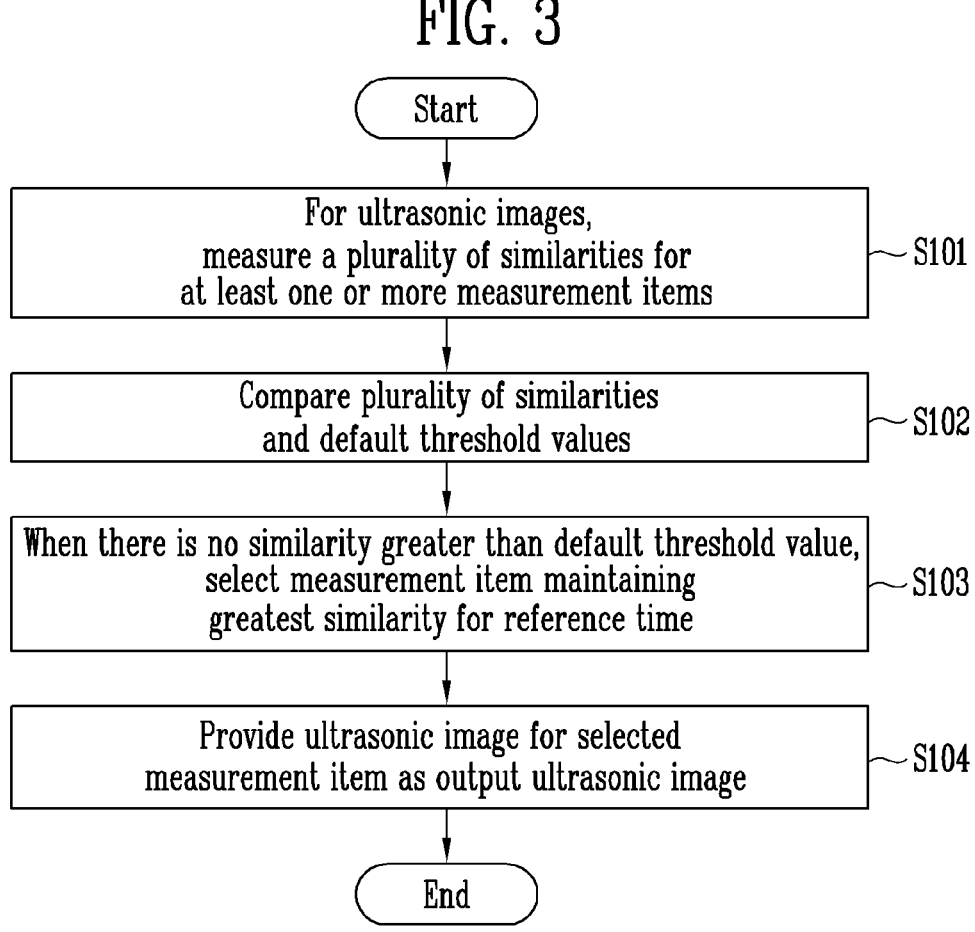
FIGS. 3 and 4 are diagrams illustrating an ultrasonic image providing method according to an embodiment of the present disclosure.
Figure 4:
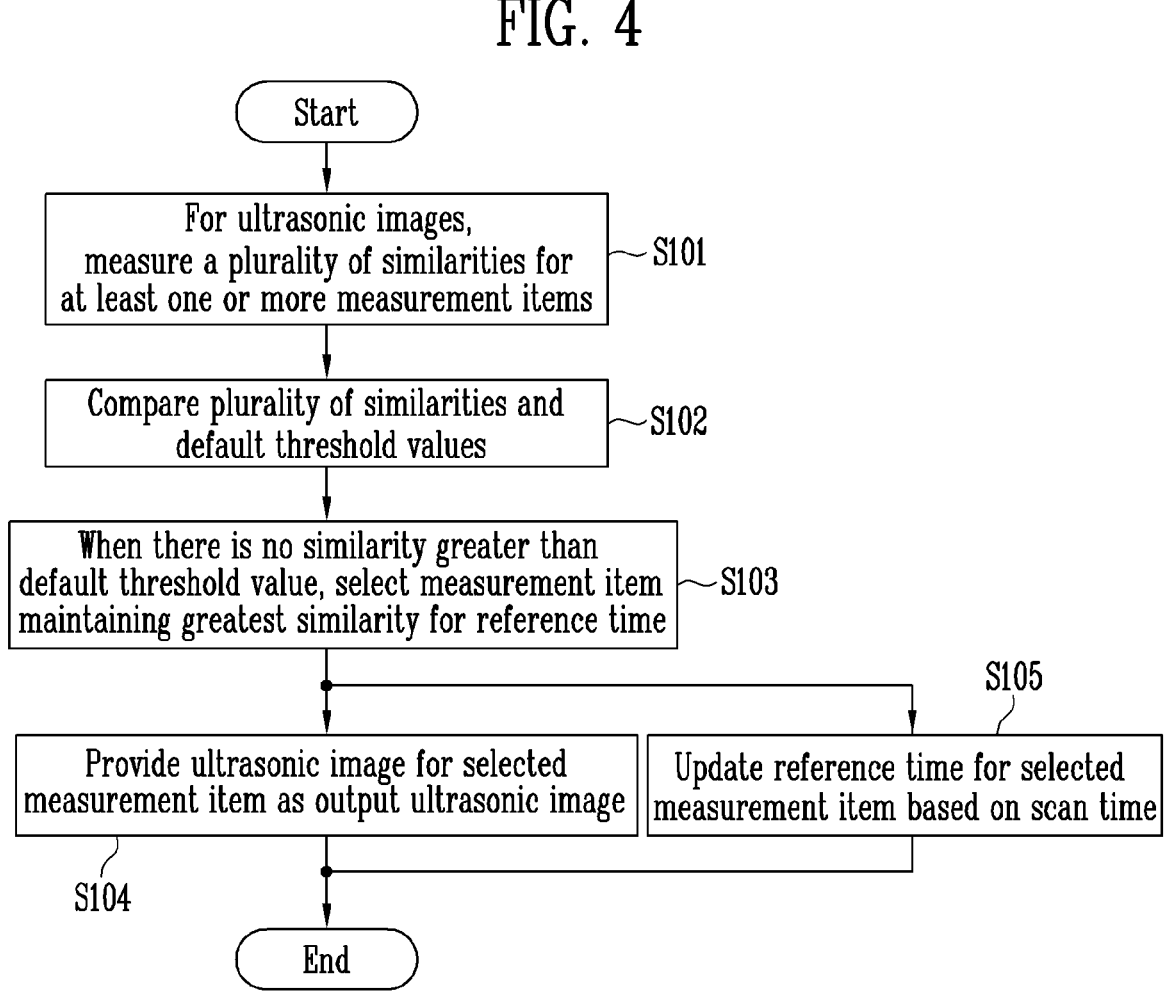

FIGS. 3 and 4 are diagrams illustrating an ultrasonic image providing method according to an embodiment of the present disclosure.

As described above, in general, the image processing unit 130 may generate ultrasonic images using ultrasonic data generated by the ultrasonic reception unit 115, and the display unit 140 may display the ultrasonic images time-sequentially. Accordingly, the user may view the display unit 140 and manually select an ultrasonic image that meets the cross-section selection criterion from among ultrasonic images.

However, hereinafter, embodiments in which the image to processing unit 130 automatically selects an ultrasonic image that meets the user's cross-section selection criterion will be described. In such embodiments, the image processing unit 130 may first generate ultrasonic images using ultrasonic data and provide the ultrasonic image that satisfies the condition among the ultrasonic images as an output ultrasonic image. The display unit 140 may display the received ultrasonic image as a still image on a portion of the display screen.

First, the image processing unit 130 may measure a plurality of similarities for at least one or more measurement items for ultrasonic images S101.

The ultrasonic images may be images generated in time order as the user scans the object 10 using the probe 20. In another example, ultrasonic images may be previously stored in the storage unit 150 or may be received from an external device through the communication unit 160.

A plurality of measurement items may be dimensions or indices of some or all of the object 10. For example, the plurality of measurement items may correspond to at least one of the length, circumference, thickness, area, volume, and index of some or all of the object 10. For example, when the object 10 is all or part of the uterus or fetus, measurement items may be head circumference HC, 4-chamber view 4CV, amniotic fluid index AFI, abdomen, femur length FL, etc.

The similarity for the measurement item of the ultrasonic image may mean a confidence level when the corresponding measurement item is measured using the corresponding ultrasonic image. The similarity may be determined by a machine trained classifier, or may be determined using an algorithm that considers the sum of brightness values or gradient magnitudes of a specific region, an image similarity comparison algorithm, and the like. The algorithm for determining similarity may use known algorithms of deep learning and machine learning.

Next, the image processing unit 130 may compare the plurality of similarities and the plurality of corresponding default threshold values, respectively S102.

A similarity higher than the default threshold value may indicate that the corresponding ultrasonic image is suitable for measuring the corresponding measurement item. A similarity lower than the default threshold value may indicate that a corresponding ultrasonic image is unsuitable for measuring a corresponding measurement item. However, as described above, since users have various cross-section selection criteria, it is very difficult to set a default threshold value suitable for all users in advance. In the present embodiment, the default threshold value may be a threshold value determined empirically to satisfy various users. Default threshold values may be stored in advance in the storage unit 150. Depending on embodiments, the default threshold values may be updated.

Depending on embodiments, default threshold values may be independently set for each measurement item. For example, default threshold values may be set differently for each measurement item. For example, a default threshold value may be set to 0.8 for head circumference and a default threshold value may be set to 0.7 for a 4-chamber view. In some cases, some default threshold values may be set equal to each other.

Next, when none of the plurality of similarities is greater than the corresponding default threshold value, the image processing unit 130 may select a measurement item maintaining the greatest similarity among the plurality of similarities for a reference time S103.

For example, there may be a case in which an ultrasonic image having a low similarity for a measurement item is provided to the user, such as a shadow appearing on the ultrasonic image due to the position of the fetus. Here, the user determines that the position of the fetus cannot be easily changed, and may increase the scan time of the probe 20 with a will to acquire a corresponding ultrasonic image (or a slightly better ultrasonic image) even though the similarity is low.

In other words, a measurement item that maintains the greatest similarity among the plurality of similarities for the reference time may be a measurement item that the user has a will to measure. For example, when it is determined that the similarity of the head circumference is 0.55, the similarity of the 4-chamber view is 0.5, and the similarity of the femur length is 0.4 for the ultrasonic images within the reference time, the image processing unit 130 may select the head circumference as a measurement item.

Depending on embodiments, the reference time may be independently set for each user. For example, the reference time may be set differently for each user. Depending on embodiments, the reference time for each of the plurality of measurement items may be set independently of each other. For example, reference times for each of the plurality of measurement items may be different for each other.

Next, the image processing unit 130 may provide an ultrasonic image for the selected measurement item as an output ultrasonic image. In one embodiment, the image processing unit 130 may provide at least one of ultrasonic images photographed (generated) for the reference time as an output ultrasonic image for a selected measurement item.

In one embodiment, the image processing unit 130 may provide an ultrasonic image having the highest similarity for the selected measurement item among ultrasonic images photographed (generated) for the reference time as an output ultrasonic image. In another embodiment, the image processing unit 130 may provide an ultrasonic image selected by using statistics such as a maximum value (max), an average value (mean), and a median value (median) for a selected measurement item among ultrasonic images photographed (generated) for the reference time as an output ultrasonic image. In another embodiment, the image processing unit 130 may provide an ultrasonic image selected by using statistics such as max, mean and median for a selected measurement item among ultrasonic images having a similarity of a certain level or higher for the selected measurement item as an output ultrasonic image.

According to the embodiment of FIG. 3, the image processing unit 130 may, by setting an independent reference time for each user, reflect the cross-section selection criteria of each user, and automatically provide an ultrasonic image for a measurement item.

Referring to FIG. 4, the image processing unit 130 may update the reference time for the selected measurement item based on the scan time for which the greatest similarity is maintained S105. In one embodiment, the reference time may be updated to be longer as the scan time increases, and the reference time may be updated to be shorter as the scan time decreases.

For example, a user used an average of 20 seconds to scan the head circumference with the probe 20 in the past, but may use an average of 15 seconds to scan the head circumference now. In addition, while the first user uses an average of 17 seconds to scan the head circumference with the probe 20, the second user may use an average of 12 seconds to scan the head circumference.

According to the present embodiment, by setting a user-customized reference time, it is possible to automatically provide an ultrasonic image for a measurement item by reflecting the cross-section selection criteria of each user.

Default threshold values and reference time may be stored in the storage unit 150 or received from an external device through the communication unit 160.

In one embodiment, for the selected measurement item, when an ultrasonic image having a higher similarity than the greatest similarity is added, the image processing unit 130 may update the output ultrasonic image with the added ultrasonic image. Accordingly, it is possible to help a user to more easily measure measurement items.

In one embodiment, the image processing unit 130 may provide an indicator indicating that the similarity of the selected measurement item is lower than a default threshold value for the provided ultrasonic image. Accordingly, it is possible to give the user a choice whether to search for more ultrasonic images having a higher similarity or to perform a diagnosis using the provided output ultrasonic image.

Figure 5:
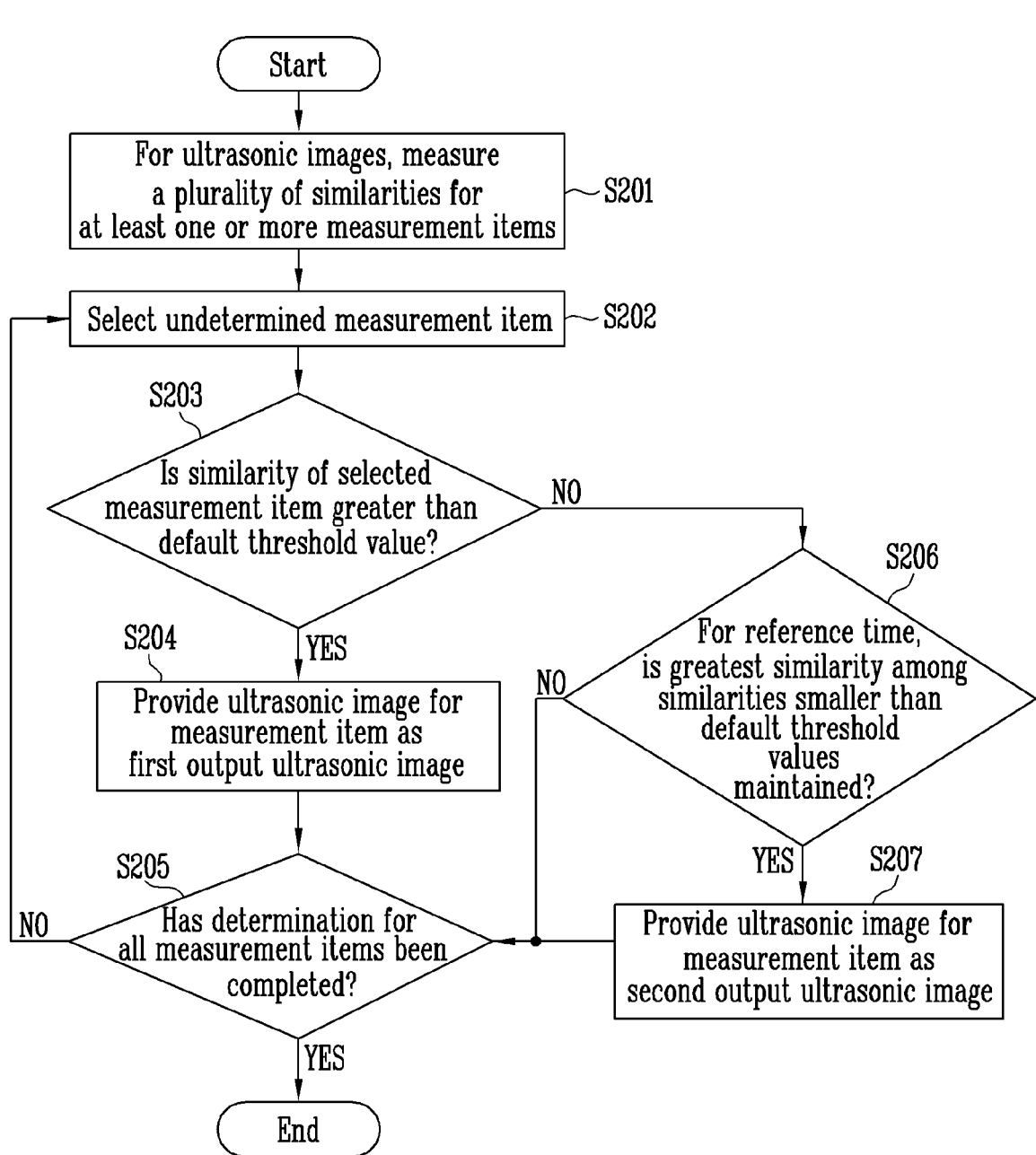
Figure 7:
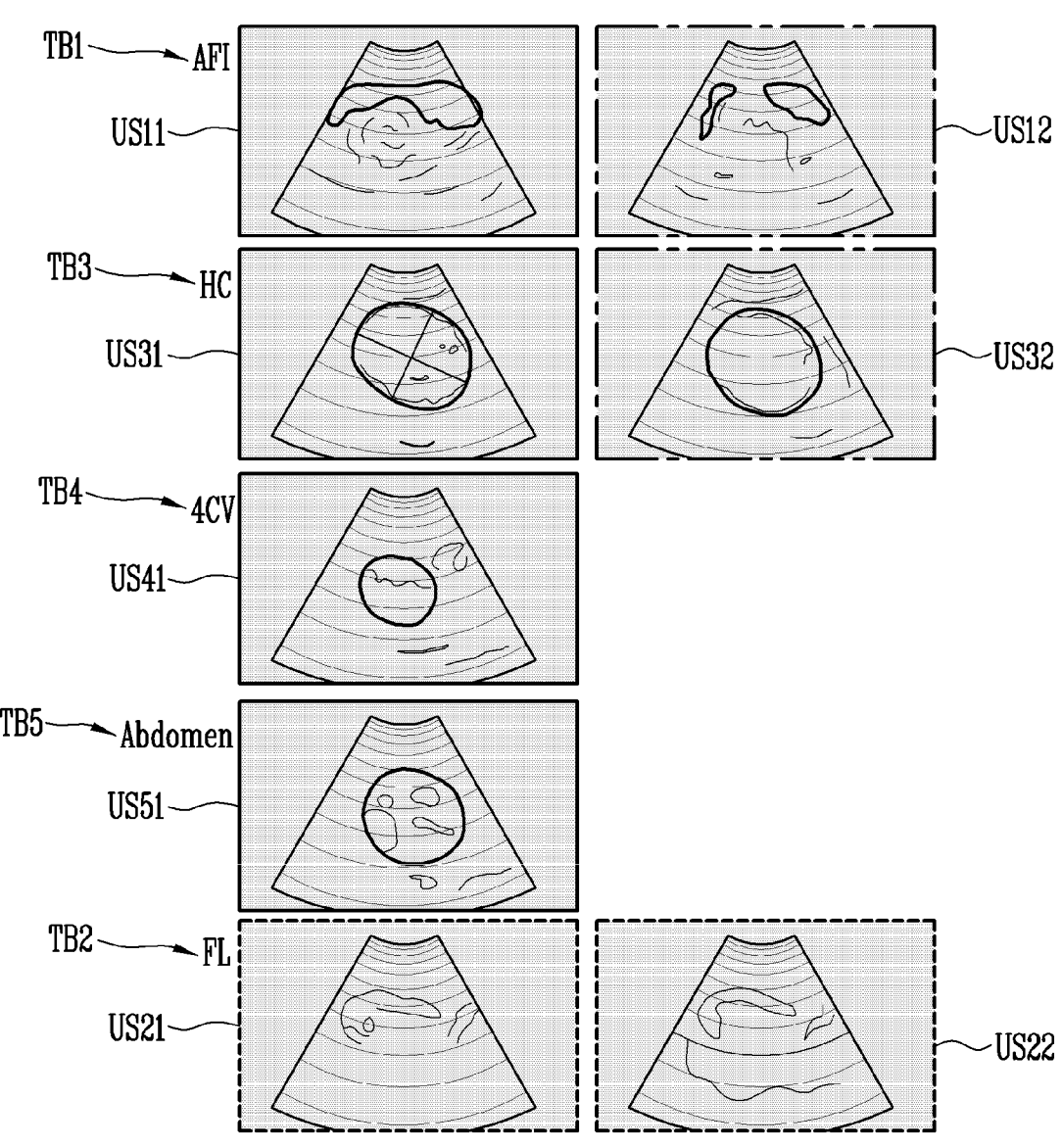
FIG. 7 is a diagram illustrating a display screen of a display unit according to an embodiment of the present disclosure.

FIGS. 5 and 6 are diagrams illustrating an ultrasonic image providing method according to another embodiment of the present disclosure. FIG. 7 is a diagram illustrating a display screen of a display unit 140 according to an embodiment of the present disclosure.

First, the image processing unit 130 may measure a plurality of similarities for at least one or more measurement items for ultrasonic images S201. Since step S201 is the same as step S101 described with reference to FIG. 3, duplicate descriptions will be omitted.

Next, the image processing unit 130 may compare the plurality of similarities and the plurality of corresponding default threshold values, respectively. Among the descriptions of this step, a duplicate description of the same part as the step S102 described with reference to FIG. 3 will be omitted. Specifically, the image processing unit 130 may select a measurement item that has not yet been determined S202, and determine whether the similarity of the selected measurement item is greater than a default threshold value S203.

If the similarity (e.g., first similarity) of the selected measurement item (e.g., first measurement item) is greater than the default threshold value (e.g., first default threshold) S203, the image processing unit 130 may provide the ultrasonic image for the selected measurement item as a first output ultrasonic image S204. For example, the image processing unit 130 may provide a first ultrasonic image for the first measurement item having the first similarity greater than the first default threshold value as a first output ultrasonic image. For example, the first measurement item TB1 may be an amniotic fluid index AFI, and the display unit 140 may display a first ultrasonic image US12 for the amniotic fluid index AFI on a part of the display screen (See FIG. 7).

Next, the image processing unit 130 may confirm whether the determination for all measurement items has been completed S205. For example, when it is confirmed that the determination for the femur length has not yet been completed, the image processing unit 130 may select the femur length as a measurement item to be determined S202.

Next, if the similarity (e.g., second similarity) of the selected measurement item (e.g., second measurement item) is smaller than the default threshold value (e.g., second default threshold value) S203, the image processing unit 130 may determine whether the selected measurement item maintains the greatest similarity (e.g., second similarity) among similarities smaller than default threshold values for a reference time S206.

For example, when the default threshold value of the sixth measurement item is set to 0.8, the default threshold value of the seventh measurement item is set to 0.81, the default threshold value of the femur length is set to 0.82, and for each reference time, the similarity of the sixth measurement item is determined to be 0.5, the similarity of the seventh measurement item is determined to be 0.55, and the similarity of the femur length is determined to be 0.6, the image processing unit 130 may determine that the femur length maintained the greatest similarity.

Accordingly, the image processing unit 130 may provide an ultrasonic image for a measurement item (e.g., femur length) as a second output ultrasonic image S207. In other words, the image processing unit 130 may, after the first ultrasonic image is provided, provide a second ultrasonic image for a second measurement item maintaining the greatest second similarity among similarities smaller than default threshold values for a reference time as a second output ultrasonic image. For example, the second measurement item TB2 may be the femur length FL, and the display unit 140 may display the second ultrasonic image US22 for the femur length FL on a part of the display screen (See FIG. 7).

The image processing unit 130 may repeat the above-described steps until it completes the determination for all measurement items S205, S202. Referring to FIG. 7, a case in which a third ultrasonic image US32 is provided since the similarity of the head circumference HC which is the third measurement item TB3 is determined to exceed the third default threshold value, a fourth ultrasonic image US41 is provided since the similarity of the f4-chamber view 4CV which is the fourth measurement item TB4 is determined to exceed the fourth default threshold value, and a fifth ultrasonic image US51 is provided since the similarity of the abdomen which is the fifth measurement item TB5 is determined to exceed the fifth default threshold value is shown as an example.

According to an embodiment of FIG. 5, the image processing unit 130 may, by setting an independent reference time for each user, reflect the cross-section selection criteria of each user to automatically provide an ultrasonic image for a measurement item.

Referring to FIG. 6, the image processing unit 130 may update the reference time for the second measurement item based on the scan time for which the second similarity is maintained S208. In one embodiment, the reference time may be updated to be longer as the scan time increases, and the reference time may be updated to be shorter as the scan time decreases.

Reference times for each of the plurality of measurement items may be different from each other. Reference times for each of the plurality of users may be different from each other. According to the present embodiment, by setting a user-customized reference time, it is possible to automatically provide an ultrasonic image for a measurement item by reflecting the cross-section selection criteria of each user.

Default threshold values and reference time may be stored in the storage unit 150 or received from an external device through the communication unit 160.

In one embodiment, for the first measurement item TB1, when an ultrasonic image US11 having a higher similarity than the first similarity is added, the image processing unit 130 may update the first output ultrasonic image (i.e., first ultrasonic image US12) with the added ultrasonic image US11. Accordingly, it is possible to help the user to more easily measure measurement items.

For example, as shown in FIG. 7, the display unit 140 may, by simultaneously displaying the ultrasonic image US11 and the first ultrasonic image US12, give the user an option for diagnosis. In another example, the display unit 140 may display only the ultrasonic image US11 without displaying the first ultrasonic image US12 any longer. In the example of FIG. 7, the added ultrasonic image US31 is displayed for the third measurement item TB3 as well.

In one embodiment, for the second measurement item TB2, when an ultrasonic image US21 having a higher similarity than the second similarity is added, the image processing unit 130 may update the second output ultrasonic image (i.e., second ultrasonic image US22) with the added ultrasonic image US21. Accordingly, it is possible to help the user to more easily measure measurement items.

In one embodiment, the image processing unit 130 may, for the first ultrasonic image US12, provide a first indicator (e.g., dashed-dotted line border of US12) indicating that the first similarity is higher than the first default threshold value. In one embodiment, the image processing unit 130 may, for the second ultrasonic image US22, provide a second indicator (e.g., dotted line border of US22) indicating that the second similarity is lower than the second default threshold value. In one embodiment, for the added ultrasonic image US11, the image processing unit 130 may provide a third indicator (e.g., solid line border of US11) indicating that the similarity (e.g., third similarity) is higher than the first similarity. Accordingly, it is possible to give the user a choice whether to search for more ultrasonic images having a higher similarity or to perform a diagnosis using the provided ultrasonic images.

Figure 8:
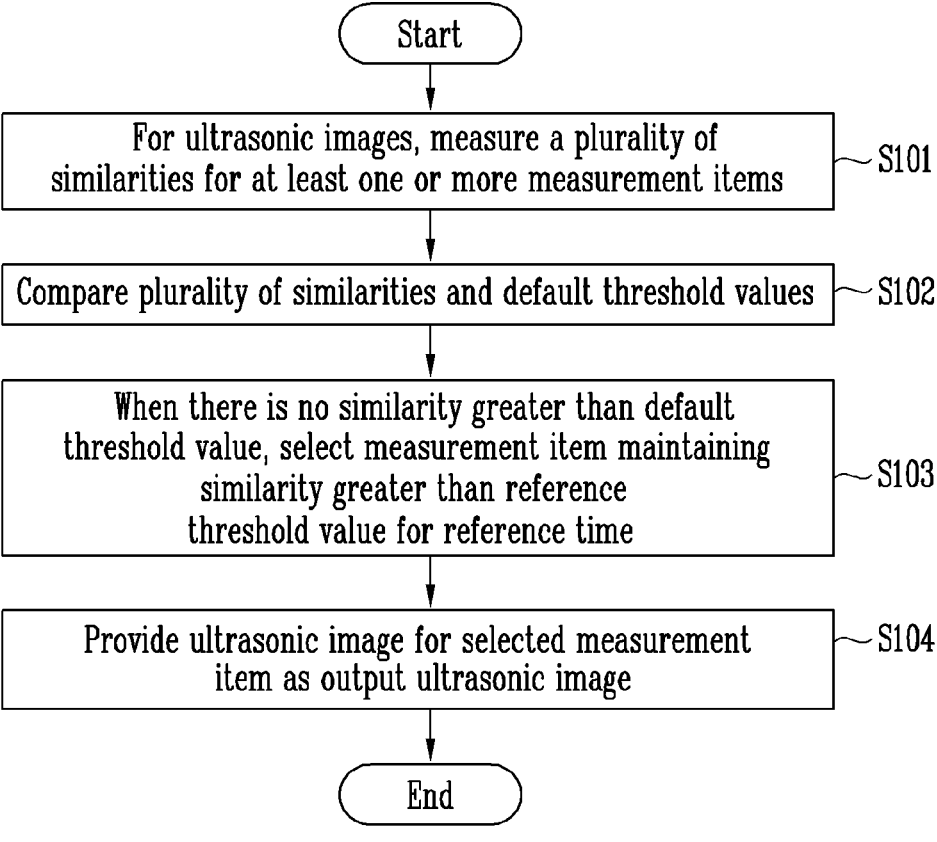

FIGS. 8 and 9 are diagrams illustrating an ultrasonic image providing method according to another embodiment of the present disclosure.

Referring to the embodiment of FIG. 8, the image processing unit 130 may measure a plurality of similarities for at least one or more measurement items for ultrasonic images S101. Next, the image processing unit 130 may compare the plurality of similarities and the plurality of corresponding default threshold values, respectively S102. Next, when none of the plurality of similarities is greater than the corresponding default threshold value, the image processing unit 130 may select a measurement item maintaining a similarity greater than the reference threshold value for a reference time S103'. Next, the image processing unit 130 may provide an ultrasonic image for the selected measurement item as an output ultrasonic image S104.

Since steps S101, S102, S104, and S105 of the embodiment of FIGS. 8 and 9 are the same as those described with reference to FIGS. 3 and 4, duplicate descriptions will be omitted. In addition, since all contents described with reference to FIGS. 3 and 4 can be applied to the embodiments of FIGS. 8 and 9, duplicate descriptions will be omitted.

Referring to step S103' of FIG. 8, compared to step S103 of FIG. 3, a condition of a reference threshold value is added. The reference threshold value may be smaller than the default threshold value. The reference threshold value may be set independently for each user. For example, the reference threshold value may be set differently for each user. The reference threshold value may be set independently for each measurement item. For example, the reference threshold value may be set differently for each measurement item. The reference threshold value may be stored in the storage unit 150.

According to an embodiment of FIG. 8, the image processing unit 130 may, by setting independent reference threshold values for each user, reflect the cross-section selection criteria of each user to automatically provide an ultrasonic image for a measurement item.

Referring to FIG. 9, the image processing unit 130 may update the reference threshold value for the selected measurement item based on the similarity of the selected measurement item S106. In one embodiment, the reference threshold value may be updated to increase as the similarity increases, and the reference threshold value may be updated to decrease as the similarity decreases.

The reference threshold value may be smaller than the default threshold value at both a point in time before the update and a point in time after the update. According to the present embodiment, by setting a user-customized reference threshold value, it is possible to automatically provide an ultrasonic image for a measurement item by reflecting the cross-section selection criteria of each user.

Figure 10:
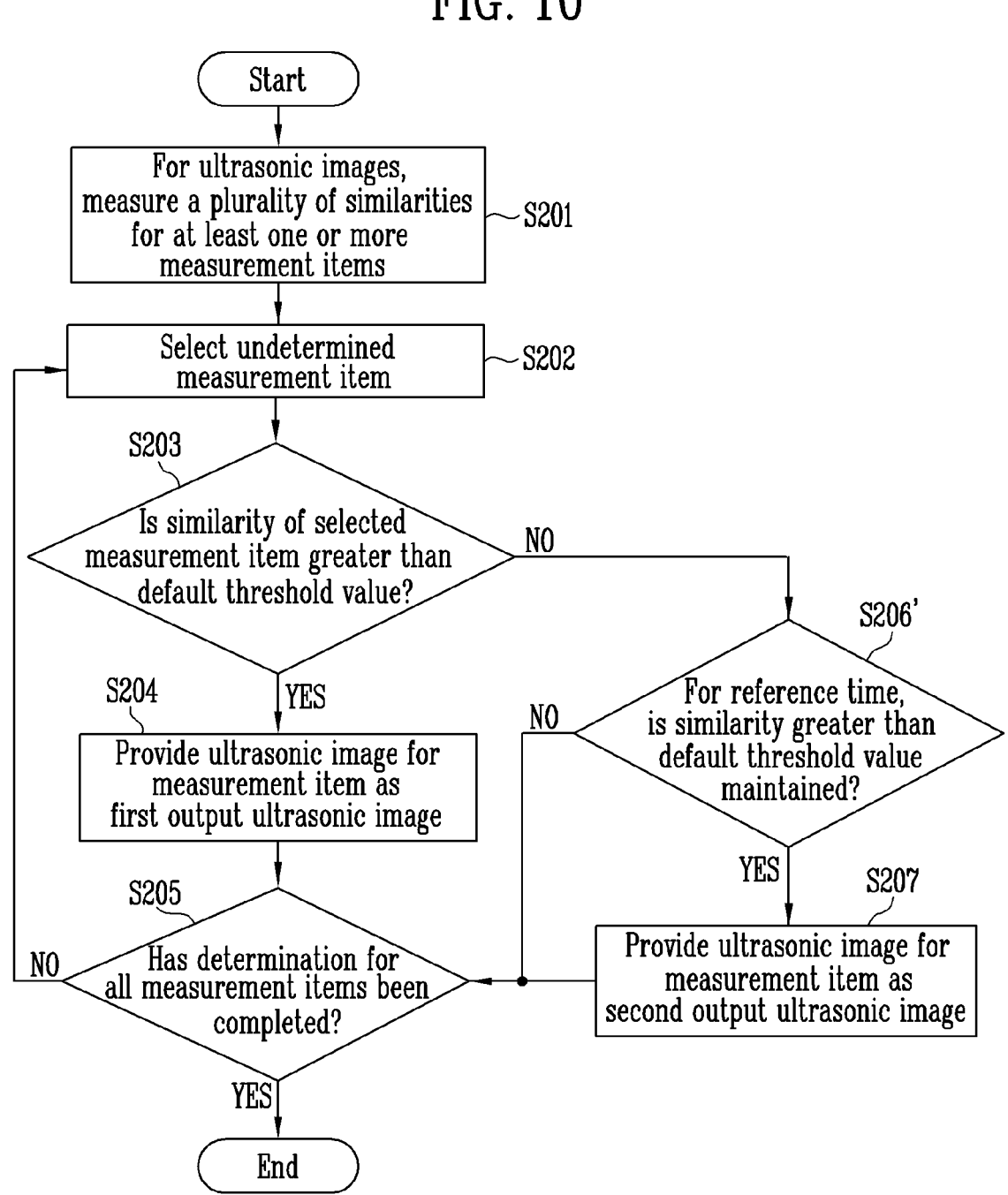

FIGS. 10 and 11 are diagrams illustrating an ultrasonic image providing method according to another embodiment of the present disclosure.

Referring to an embodiment of FIG. 10, the image processing unit 130 may measure a plurality of similarities for at least one or more measurement items for ultrasonic images S201. The image processing unit 130 may compare the plurality of similarities and the plurality of corresponding default threshold values, respectively S202, S203, S205. The image processing unit 130 may provide a first ultrasonic image for a first measurement item having a first similarity greater than a first default threshold value as a first output ultrasonic image S204. After the first ultrasonic image is provided, the image processing unit 130 may provide a second ultrasonic image for a second measurement item maintaining a second similarity greater than a reference threshold value and smaller than a second default threshold value for a reference time as a second output ultrasonic image S206', S207.

Since steps S201, S202, S203, S204, S205, S207 and S208 of the embodiment of FIGS. 10 and 11 are the same as those described with reference to FIGS. 5, 6 and 7, duplicate descriptions will be omitted. In addition, since all contents described with reference to FIGS. 5, 6, and 7 can be applied to the embodiments of FIGS. 10 and 11, duplicate descriptions will be omitted.

Referring to step S206' of FIG. 10, compared to step S206 of FIG. 5, a condition of a reference threshold value is added. The reference threshold value may be smaller than the default threshold value. The reference threshold value may be set independently for each user. For example, the reference threshold value may be set differently for each user. The reference threshold value may be set independently for each measurement item. For example, the reference threshold value may be set differently for each measurement item. The reference threshold value may be stored in the storage unit 150.

According to an embodiment of FIG. 10, the image processing unit 130 may, by setting independent reference threshold values for each user, reflect the cross-section selection criteria of each user to automatically provide an ultrasonic image for a measurement item.

Referring to FIG. 11, the image processing unit 130 may update the reference threshold value for the second measurement item based on the second similarity S209. In one embodiment, the reference threshold value may be updated to increase as the second similarity increases, and the reference threshold value may be updated to decrease as the second similarity decreases. The reference threshold value may be smaller than the default threshold value at both a point in time before the update and a point in time after the update. According to the present embodiment, by setting a user-customized reference threshold value, it is possible to automatically provide an ultrasonic image for a measurement item by reflecting the cross-section selection criteria of each user.

Figure 12:
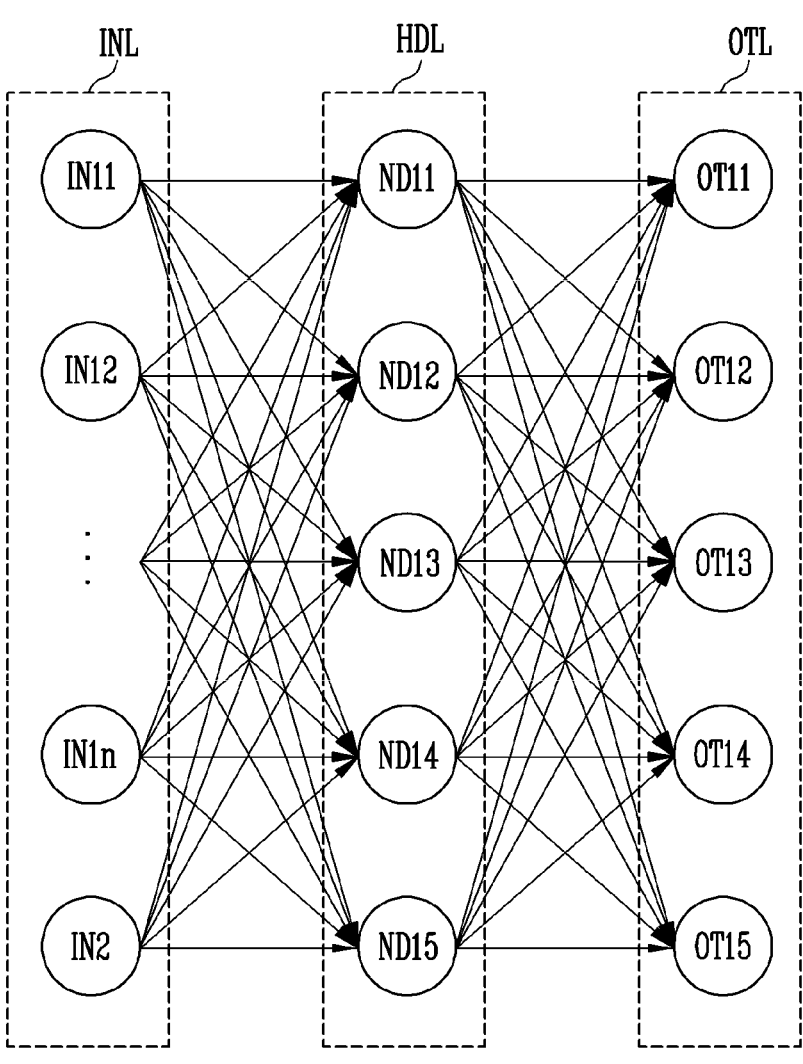
FIGS. 12 and 13 are diagrams illustrating a learning algorithm according to an embodiment of the present disclosure.
Figure 13:
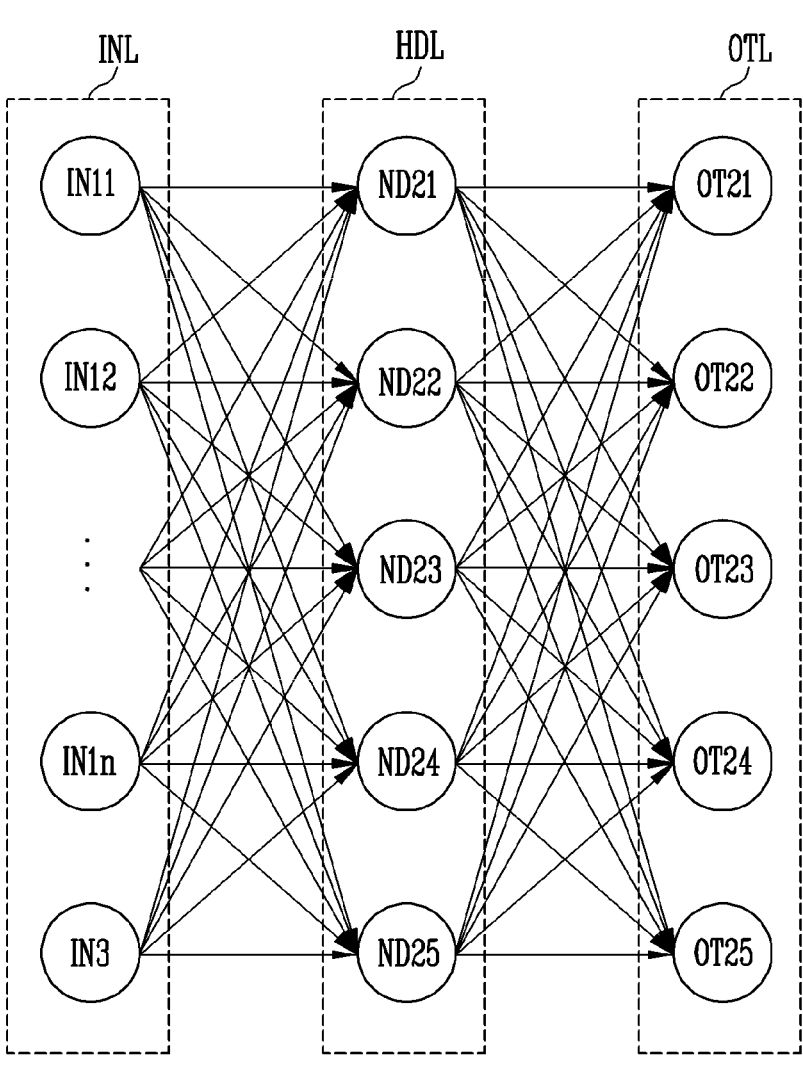

FIGS. 12 and 13 are diagrams illustrating a learning algorithm according to an embodiment of the present disclosure.

Referring to FIG. 12, a learning algorithm including at least one hidden layer HDL between an input layer INL and an output layer OTL is shown as an example.

The learning algorithm may be recorded on a recording medium and executed by the ultrasound diagnosis apparatus 100. The recording medium may correspond to the storage unit 150 of the ultrasound diagnosis apparatus 100. Meanwhile, the recording medium is embedded in an external server of the ultrasound diagnosis apparatus 100, and the ultrasound diagnosis apparatus 100 may execute the learning algorithm by communicating with the external server through the communication unit 160.

The recording medium includes all types of recording devices capable of storing data, algorithms, or programs that can be read by a computer system. Examples of computer-readable recording media include ROM, RAM, CD-ROM, magnetic tape, floppy disk, optical data storage device, hard disk, external hard disk, SSD, USB storage device, DVD, Blu-ray disk, etc. In addition, the computer-readable recording medium may be a combination of a plurality of devices or may be distributed in computer systems connected through a network. Such a recording medium may be a non-transitory computer readable medium. A non-transitory computer-readable recording medium is a medium that stores data or programs semi-permanently and is readable by a computer, rather than a medium that stores data or programs for a short moment, such as a register, cache, or memory.

The input layer INL may include first inputs IN11, IN12, . . . , IN1n, and a second input IN2. The hidden layer HDL may include a plurality of nodes ND11, ND12, ND13, ND14, ND15. The output layer OTL may include first outputs OT11, OT12, OT13, OT14, OT15. The number of inputs, nodes, and outputs may vary depending on embodiments. In addition, whether all layers will be fully connected or connected in another way may vary depending on embodiments. The learning algorithm of the present embodiment may be referred to as shallow learning or deep learning depending on the number of hidden layers HDL.

The learning algorithm may include receiving ultrasonic images as first inputs IN11~IN1n of the input layer INL. In addition, the learning algorithm may include receiving information about ultrasonic images that maintain a similarity for a first reference time among ultrasonic images as a second input IN2 of the input layer INL.

In addition, the learning algorithm may include, based on the first inputs IN11~IN1n and the second input IN2, providing whether the ultrasonic images include at least one or more measurement items as a first output of the output layer OTL. In FIG. 11, it is assumed that the output layer OTL includes first outputs OT11~OT15 for the plurality of measurement items.

The relationship between the first inputs IN11~IN1n, the second input IN2, and the first outputs OT11~OT15 may be determined by connection relationships between the layers INL, HDL, OTL, weights, biases, etc.

For example, it is assumed that the first outputs OT11~OT15 respectively correspond to head circumference HC, 4-chamber view 4CV, amniotic fluid index AFI, abdomen, and femur length FL. Here, if the first output OT11 is 0, the first output OT12 is 1, the first output OT13 is 0, the first output OT14 is 0, and the first output OT15 is 0, the learning algorithm may determine that the ultrasonic images correspond to the 4-chamber view 4CV.

According to one embodiment, the first reference time may be information about a first user among a plurality of users. Here, the learning algorithm may further include modifying the hidden layer HDL by receiving first reward information of the first user as feedback for the first output (e.g, first outputs OT11~OT15).

The first reward information is information provided by the first user by observing the first outputs OT11~OT15, and may be information indicating that the first outputs OT11~OT15 are correct conclusions or incorrect conclusions.

Modifying the hidden layer HDL means modifying at least one of connection relationships between the aforementioned layers NL, HDL, OTL, weights, and biases.

The ultrasound diagnosis apparatus 100 may provide at least one of the ultrasonic images as an ultrasonic image for measurement items indicated by the first outputs OT11~OT15. According to the present embodiment, a customized ultrasonic image may be provided to the first user by reflecting the first reference time and the similarity for the measurement item, which are subjective criteria of the first user.

Referring to FIG. 13, a learning algorithm for a second user is exemplary illustrated. In describing FIG. 13, descriptions of overlapping contents with those of FIG. 12 will be omitted.

The input layer INL may include first inputs IN11, IN12, . . . , IN1n, and a third input IN3. The hidden layer HDL may include a plurality of nodes ND21, ND22, ND23, ND24, ND25. The output layer OTL may include second outputs OT21, OT22, OT23, OT24, OT25. The number of inputs, nodes, and outputs may vary depending on embodiments.

The learning algorithm of the present embodiment may include receiving information about ultrasonic images that maintain a similarity for a second reference time among ultrasonic images as a third input IN3 of the input layer INL. In addition, the learning algorithm may further include, based on the first inputs IN11~IN1n and the third input IN3, providing whether the ultrasonic images correspond to at least one or more measurement items as a second output (e.g., second outputs OT21~OT25) of the output layer OTL.

The second reference time may be information about a second user among a plurality of users. The second user is a different person from the first user. The learning algorithm may further include modifying the hidden layer HDL by receiving second reward information of the second user as feedback for the second output (e.g, second outputs OT21~OT25).

According to the present embodiment, the learning algorithm may provide different outputs according to users for the same first inputs IN11~IN1n. According to the present embodiment, for each of the plurality of users, a customized ultrasonic image may be provided by reflecting the reference time and the similarity for the measurement item which are subjective criteria.

According to one embodiment of the present disclosure, the learning algorithm may further include updating the first reference time based on the scan time (e.g., the probe scan time of the first user) for which the similarity is maintained.

Similarly, the learning algorithm may further include updating the second reference time based on the scan time (e.g., the probe scan time of the second user) for which the similarity is maintained.

According to one embodiment of the present disclosure, the learning algorithm may further include updating the first reference time based on a difference between a point in time when the last image is input and a point in time when the first image is input among the ultrasonic images which maintain the similarities. Similarly, the learning algorithm may further include updating the second reference time based on a difference between a point in time when the last image is input and a point in time when the first image is input among the ultrasonic images which maintain the similarities.

The drawings referred to so far and detailed description of the disclosure are merely illustrative of the present disclosure, which is only used for the purpose of explaining the present disclosure and is not used to limit meaning or limit the scope of the present disclosure described in the claims. Therefore, those skilled in the art will understand that various modifications and equivalent other embodiments are possible therefrom. Therefore, the true technical protection scope of the present disclosure should be determined by the technical spirit of the appended claims.

The invention claimed is:

1. An ultrasonic image providing method comprising:

obtaining a plurality of ultrasound images based on receiving a user input of scanning an object using a probe for a reference time, each of the plurality of ultrasound images including a plurality of anatomical structures, calculating similarities of the plurality of anatomical structures for each of the plurality of ultrasound images, wherein a similarity of an anatomical structure for an ultrasound image represents a confidence level of a measurement value when the anatomical structure is measured using the ultrasound image;

selecting, among the plurality of anatomical structures, an anatomical structure maintaining a greatest similarity among the similarities calculated for each of the plurality of ultrasound images for the reference time, as an anatomical structure to be measured;

determining an output ultrasound image for measuring the selected anatomical structure, based on similarities of the selected anatomical structure corresponding to the plurality of ultrasound images, among the plurality of ultrasound images; and displaying the output ultrasound image as an ultrasound image for measuring the selected anatomical structure and an image indicating the selected anatomical structure on the output ultrasound image.

2. The ultrasonic image providing method of claim 1, further comprising:

updating the reference time for the selected anatomical structure based on a scan time for which the greatest similarity is maintained.

3. The ultrasonic image providing method of claim 2, wherein the reference time for each of the plurality of anatomical structures is different from each other.

4. The ultrasonic image providing method of claim 1, further comprising:

for the selected anatomical structure, when an ultrasound image having a higher similarity than the greatest similarity is added, updating the output ultrasound image with the added ultrasound image.

5. The ultrasonic image providing method of claim 1, further comprising:

for the provided output ultrasound image, providing an indicator indicating that the similarity of the selected anatomical structure is lower a default threshold value.

6. The ultrasonic image providing method of claim 1, further comprising:

when none of the similarities of the plurality of anatomical structures is greater than corresponding default threshold value, selecting aan anatomical structure maintaining a similarity greater than a reference threshold value for the reference time; and providing an ultrasound image for the selected anatomical structure as the output ultrasound image.

7. The ultrasonic image providing method of claim 6, further comprising:

updating the reference time for the selected anatomical structure based on a scan time for which the similarity of the selected anatomical structure is maintained and wherein the reference time and the reference threshold value for each of the anatomical structures are different from each other.

8. The ultrasonic image providing method of claim 7, further comprising:

updating the reference threshold value for the selected anatomical structure based on the similarity of the selected anatomical structure and wherein the reference threshold value is smaller than the default threshold value at both a point in time before the update and a point in time after the update.

9. The ultrasonic image providing method of claim 6, further comprising:

for the selected anatomical structure, when an ultrasound image having a higher similarity than the similarity is added, updating the output ultrasound image with the added ultrasound image.

10. The ultrasonic image providing method of claim 6, further comprising:

for the provided output ultrasound image, providing an indicator indicating that the similarity of the selected anatomical structure is lower than the default threshold value.

11. The ultrasonic image providing method of claim 1, further comprising receiving the plurality of ultrasound images as first inputs of an input layer of a learning algorithm;

receiving information about ultrasound images which maintain a similarity for a first reference time among the plurality of ultrasound images as a second input of the input layer of the learning algorithm; and based on the first inputs and the second input, providing whether the plurality of ultrasound images include at least one or more anatomical structures as a first output of an output layer.

12. The ultrasonic image providing method of claim 11, wherein the learning algorithm further comprises:

updating the first reference time based on a scan time for which the similarity is maintained and updating the first reference time based on a difference between a point in time a last image is input and a point in time when a first image is input among the ultrasound images which maintain the similarity.

13. An ultrasound imaging apparatus comprising:

an ultrasonic transceiver;

a display unit; and at least one processor, wherein the at least one processor is configured to control the ultrasonic transceiver to transmit an ultrasound signal to an object and receive an ultrasound echo signal reflecting from the object, obtain a plurality of ultrasound images based on receiving a user input of scanning an object using a probe for a reference time, each of the plurality of ultrasound images including a plurality of anatomical structures, calculate similarities of the plurality of anatomical structures for each of the plurality of ultrasound images, wherein a similarity of an anatomical structure for an ultrasound image represents a confidence level of a measurement value when the anatomical structure is measured using the ultrasound image, select, among the plurality of anatomical structures, an anatomical structure maintaining a greatest similarity among the similarities calculated for each of the plurality of ultrasound images for the reference time, as an anatomical structure to be measured, determine an output ultrasound image for measuring the selected anatomical structure, based on similarities of the selected anatomical structure corresponding to the plurality of ultrasound images, among the plurality of ultrasound images, and display, through the display unit, the output ultrasound image as an ultrasound image for measuring the selected anatomical structure and an image indicating the selected anatomical structure on the output ultrasound image.

14. The ultrasound imaging apparatus of claim 13, wherein the at least one processor is further configured to:

update the reference time for the selected anatomical structure based on a scan time for which the greatest similarity is maintained.

15. The ultrasound imaging apparatus of claim 14, wherein the reference time for each of the plurality of anatomical structures is different from each other.

16. The ultrasound imaging apparatus of claim 13, wherein the at least one processor is further configured to:

for the selected anatomical structure, when an ultrasound image having a higher similarity than the greatest similarity is added, update the output ultrasound image with the added ultrasound image.

17. The ultrasound imaging apparatus of claim 13, wherein the at least one processor is further configured to:

when none of the similarities of the plurality of anatomical structures is greater than corresponding default threshold value, for the displayed output ultrasound image, provide an indicator indicating that the similarity of the selected anatomical structure is lower than the default threshold value.

18. The ultrasonic image providing method of claim 1, wherein the calculating the similarities of the plurality of anatomical structures for each of the plurality of ultrasound images comprises:

calculating image similarities between each of the plurality of ultrasound images and a plurality of reference ultrasound images corresponding to the plurality of anatomical structures as the similarities of the plurality of anatomical structures.

19. The ultrasonic image providing method of claim 1, wherein the calculating the similarities of the plurality of anatomical structures for each of the plurality of ultrasound images comprises:

calculating the similarities of the plurality of anatomical structures for each of the plurality of ultrasound images, based on a sum of brightness values or gradient magnitudes of a region corresponding to each of the plurality of anatomical structures, for each of the plurality of ultrasound images.

* * * * *